US00PP27708P3

(12) United States Plant Patent
Olesen

(10) Patent No.: US PP27,708 P3
(45) Date of Patent: Feb. 28, 2017

(54) FLORIBUNDA ROSE PLANT NAMED 'POULCAS043'

(50) Latin Name: ***Rosa* hybrid**
Varietal Denomination: Poulcas043

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 182 days.

(21) Appl. No.: 14/121,287

(22) Filed: Aug. 15, 2014

(65) Prior Publication Data

US 2016/0050814 P1 Feb. 18, 2016

(51) Int. Cl.
*A01H 5/02* (2006.01)

(52) U.S. Cl.
USPC ..... Plt./144

(58) Field of Classification Search
USPC ..... Plt./144
See application file for complete search history.

*Primary Examiner* — Keith Robinson

(57) ABSTRACT

A new garden rose plant of the Floribunda class which has abundant, white flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas043'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2000 and the resulting seeds were planted in a controlled environment in Fredensborg, Denmark. The new variety, named 'Poulcas043', originated as a single seedling from the stated cross.

The new variety may be distinguished from its male pollen parent and female seed parent by the following characteristic. The female seed parent and the male pollen parent have light pink flowers, while the new plant has white flowers.

The objective of the hybridization of this rose variety was to create a new and distinct variety for garden use with unique qualities, such as:

1. Uniform and abundant white flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas043' from all other varieties of which we are aware.

As part of the rose development program, Mogens N. Olesen germinated the seeds from the aforementioned hybridization during winter of 2000 and conducted evaluations on the resulting seedlings in a controlled environment in Fredensborg, Denmark. 'Poulcas043' was selected in the spring of 2001 by the inventor as a single plant from the progeny of the aforementioned hybridization.

Asexual reproduction of 'Poulcas043' by traditional budding and rooted cuttings was first done by Mogens N. Olesen in the nursery in Fredensborg, Denmark in July, 2001. This initial and other subsequent asexual propagations conducted in controlled environments have demonstrated that the characteristics of 'Poulcas043' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcas043'.

Specifically illustrated in FIG. 1 are open flowers, petals detached, and flower buds.

Figure 1:
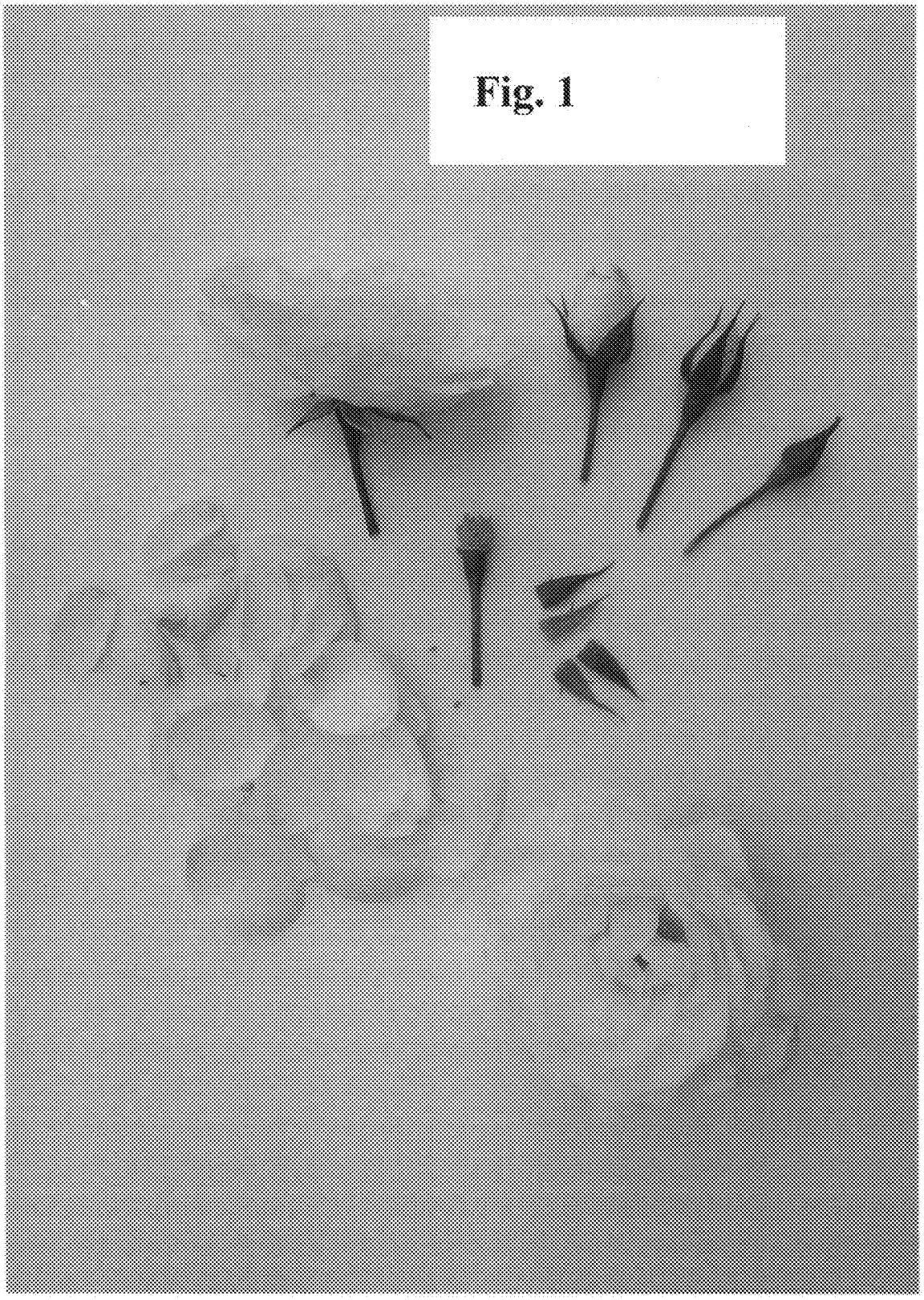
Figure 2:
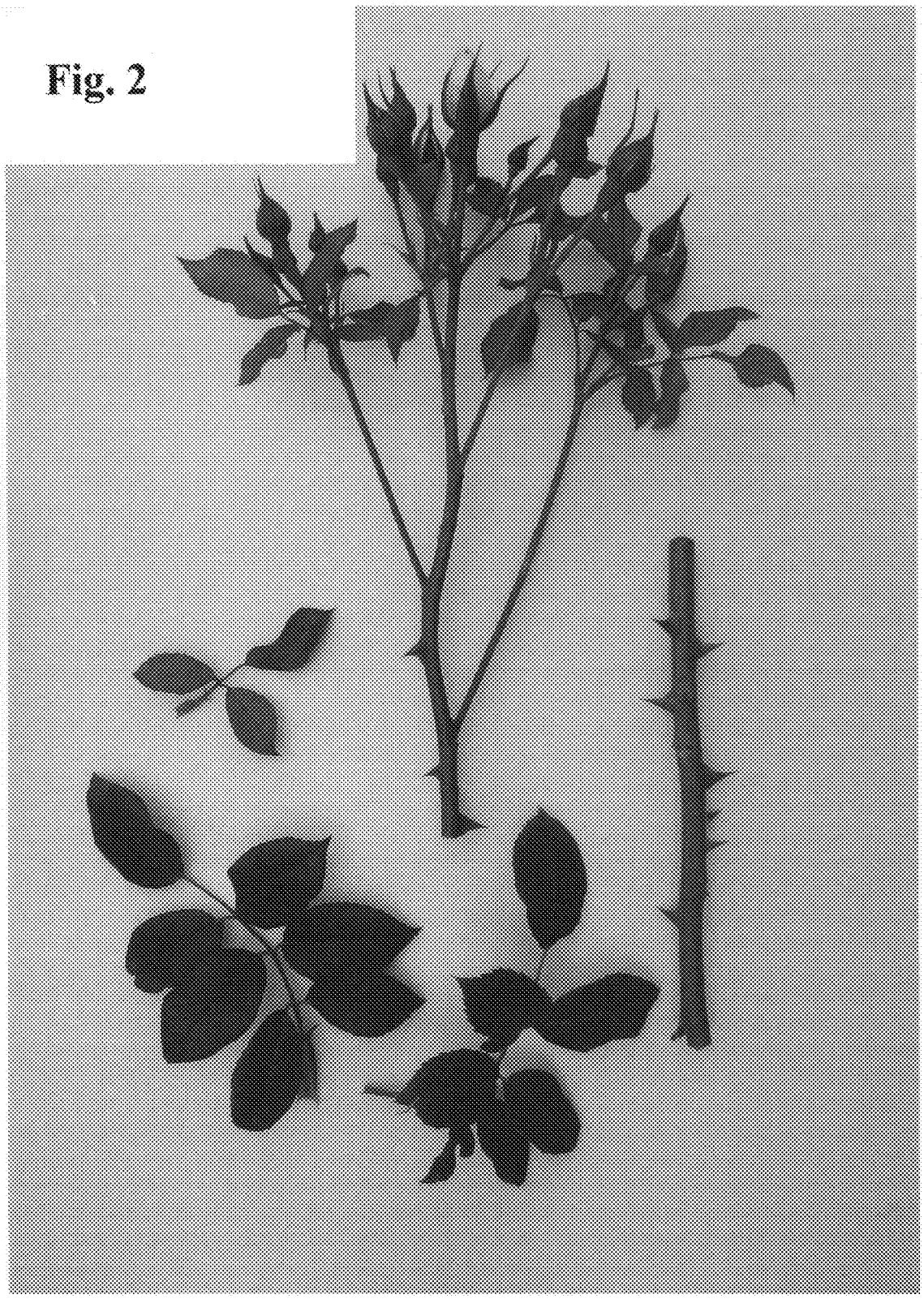
FIG. 2 shows leaves, stems, and a flowering branch.

Plants shown are 2 years of age.

DETAILED DESCRIPTION OF THE VARIETY

The following is a description of 'Poulcas043',as observed in its growth in a field nursery in Marion County, Oreg. Observed plants are 2 years of age, and were grown on their own roots. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the non-patented rose variety 'Korbin', are compared to 'Poulcas043' in Chart 1.

CHART 1

| | 'Poulcas043' | 'Korbin' |
|---|---|---|
| Petalage | about 65 | about 25 |
| Flower Diameter | 70 mm | 60 mm |
| Fragrance | None | Strong |

Flower and Flower Bud

Blooming habit: Continuous.

Flower bud:

*Size.*—Upon opening, 30 mm in length from base of receptacle to end of bud. Bud diameter is 15 mm.

*Bud form.*—Ovoid.

*Bud color.*—As sepals divide petals are White Group 155A with intonations of Yellow-Green Group 145C.

*Sepal inner surface.*—Color: Yellow-Green Group 144B. Surface: Lightly pubescent.

*Sepal outer surface.*—Color: Yellow-Green Group 144A with intonations of Greyed-Purple Group 187C. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—32 mm long, 10 mm wide.

*Receptacle.*—Texture: Smooth. Size: 10 mm in height, 7 mm wide. Color: Yellow-Green Group 144A with intonations of Greyed-Purple Group 187C. Shape: Elongated campanulate.

*Pedicel.*—Surface: Smooth. Length: 35 mm. Diameter: 3 mm on average. Color: Yellow-Green Group 146D with intonations of Greyed-Red Group 181A. Strength: Strong.

*Peduncle.*—Length: 5 to 15 cm. Diameter: 4 mm. Color: Yellow-Green Group 145A with intonations of Greyed-Red Group 181A.

Flower bud development: Flower buds are borne in panicle like clusters of 3 to 5 flower buds on each peduncle.

Flower bloom:

*Fragrance.*—None.

*Duration.*—The blooms have a duration on the plant of approximately 14 days. Petals fall cleanly away from plant after flowers have fully matured.

*Size.*—Flower diameter is 70 mm when open. Flower depth is 35 mm.

*Flower shape.*—Rosette double flowers with many slightly overlapping petals of different sizes.

*Shape of flower, side view.*—The upper portion is flat. The lower portion is concave.

Petalage: Under normal conditions, flowers have 65 petals total, 7 to 10 of which are petaloids.

General tonality of flower: Open flowers are White Group 155D.

Petal color:

*Upon opening, outer & inner petals.*—Upper surface: White Group 155D. Lower surface: White Group 155D.

*Basal petal spots.*—No distinctive coloration at the petal base observed.

*After opening, outer & inner petals.*—Upper surface: White Group 155D. Lower surface: White Group 155D.

*Basal petal spots.*—No distinctive coloration at the petal base observed.

Petals:

*Petal reflex.*—Flat.

*Margin.*—Entire and uniform. Moderate undulations.

*Shape.*—Generally rounded. Apex shape: Rounded. Base shape: Rounded.

*Size.*—40 mm (l)×40 mm (w).

*Texture.*—Smooth on upper and lower surfaces.

*Thickness.*—Average.

Petaloids:

*Size.*—17 mm (l) by 8 mm (w).

*Quantity.*—7 to 10.

*Shape.*—Elliptic. Base and apex are acute.

*Color.*—White Group 155D.

Reproductive organs:

*Pollen.*—None observed.

*Anthers.*—Size: 2 mm in length. Color: Yellow Group 6A. Quantity: 40 on average.

*Filaments.*—Color: Yellow Group 4D. Length: 11 mm.

*Pistils.*—Length: 5 mm. Quantity: 15 on average.

*Stigmas.*—Color: Green-White Group 157A.

*Styles.*—Color: Green-White Group 157A.

*Location of stigmas.*—Inferior in location relative to the length of the filaments and the height of the anthers.

*Hips.*—None Observed.

Plant

Plant growth: Upright, bushy. Plants are 100 to 120 cm in height, and 100 cm wide.

Stems:

*Color.*—Juvenile growth: Yellow-Green Group 144B with anthocyanin the color of Greyed-Orange Group 173B. Mature growth: Yellow-Green Group 144A.

*Length.*—On average, canes are 60 cm from the base of the plant to the flowering portion.

*Diameter.*—8 mm.

*Internodes.*—On mature canes, there is an average distance of 30 mm between nodes.

*Surface texture.*—Young wood: Smooth. Older wood: Smooth.

Long prickles:

*Incidence.*—10 prickles per 10 cm of stem.

*Size.*—Average length of prickles on mature stems is 9 mm.

*Shape.*—Upper portion is linear. Lower portion is concave.

*Color.*—Juvenile prickles: Greyed-Orange Group 173B. Mature prickles: Greyed-Red Group 180B.

Plant foliage:

*Compound leaf.*—180 mm (l)×111 (w).

*Quantity.*—3 leaves per 10 cm of stem on average.

*Leaf bearing angle to the stem.*—45 degrees.

*Color of juvenile foliage.*—Upper side: Yellow-Green Group 146C with intonations of Greyed-Red Group 181A. Lower side: Yellow-Green Group 146C with intonations of Greyed-Red Group 181A.

*Color of mature foliage.*—Upper side: Yellow-Green Group 147A. Lower side: Yellow-Green Group 146B.

Plant leaves and leaflets:

*Stipules.*—

*Size.*—30 mm long, 3 mm wide.

*Quantity*.—2 per compound leaf.
*Shape*.—Linear, slightly broad based with outward extending apices.
*Margins*.—Finely serrated.
*Color*.—Yellow-Green Group 147A.

Petiole:
*Length*.—40 mm.
*Diameter*.—2 mm.

Upper surface:
*Color*.—Yellow-Green Group 146B.

Lower surface:
*Color*.—Yellow-Green Group 144B.

Rachis:
*Length*.—70 mm.
*Upper surface*.—
*Color*.—Yellow-Green Group 146B.

Lower surface:
*Color*.—Yellow-Green Group 144B.
*Observations*.—Small prickles Greyed-Red Group 179B.

Leaflet:
*Quantity*.—Normally leaflets.
*Margins*.—Dentate.
*Size*.—On average terminal leaflets are 55 mm long, 40 mm wide.
*Shape*.—Generally elliptical somewhat deltoid. Base: Rounded. Apex: Cuspidate.
*Texture*.—Smooth on upper and lower surfaces.
*Thickness*.—Average.
*Arrangement*.—Odd pinnate.
*Venation*.—Reticulate.
*Glossiness*.—Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Floribunda rose class named 'Poulcas043', substantially as illustrated and described herein, due to its abundant white flowers, disease resistance, and extended period of bloom.

* * * * *